US00PP18369P2

(12) United States Plant Patent
Zaiger et al.

(10) Patent No.: US PP18,369 P2
(45) Date of Patent: Dec. 25, 2007

(54) NECTARINE TREE NAMED: 'CASCADE'

(50) Latin Name: *Prunus persica var. nucipersica*
Varietal Denomination: Cascade

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 5 days.

(21) Appl. No.: 11/500,725

(22) Filed: Aug. 9, 2006

(51) Int. Cl.
*A01H 5/00* (2006.01)

(52) U.S. Cl. ..... Plt./192

(58) Field of Classification Search ..... Plt./192
See application file for complete search history.

*Primary Examiner*—Kent Bell

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with a mild, sweet, sub-acid flavor.
2. Vigorous, upright tree growth.
3. Heavy and regular production of fruit.
4. Fruit with firm flesh, good handling and storage quality.
5. Fruit with a high degree of attractive red skin color.

1 Drawing Sheet

Botanical description: *Prunus persica* var. *nucipersica.*

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Honey Royale' (U.S. Plant Pat. No. 12,008), 'May Grand' (U.S. Plant Pat. No. 2,794), 'Ruby Gold' (U.S. Plant Pat. No. 3,101) and 'Early Sungrand' (U.S. Plant Pat. No. 1,420).

ORIGIN OF THE VARIETY

The new variety of nectarine tree (*Prunus persica* var. *nucipersica*) was originated by us in our experimental orchard located near Modesto, Calif. as a first generation cross between a proprietary selected nectarine seedling with field identification number '32RB351' and 'Honey Royale' Nectarine (U.S. Plant Pat. No. 12,008). The maternal parent (32R351) was developed from crosses between selected proprietary nectarine seedlings that originated from the following varieties 'May Grand' Nectarine (U.S. Plant Pat. No. 2,794), 'Ruby Gold' Nectarine (U.S. Plant Pat. No. 3,101) and 'Early Sungrand' Nectarine (U.S. Plant Pat. No. 1,420). The pollen originated from the commercial nectarine 'Honey Royale' (U.S. Plant Pat. No. 12,008). We planted and maintained a large group of these first generation seedlings on their own root system and under close and careful observation, we recognized the desirable fruit characteristics of the present variety and selected it in 1998 for asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus persica* var. *nucipersica*) is of large size, vigorous, upright growth and a regular and productive bearer of large size, firm, yellow flesh, freestone fruit with a mild, sweet, sub-acid flavor and excellent eating quality. The fruit is further characterized by having an attractive red skin color, firm flesh, with fruit holding firm on the tree 8 to 10 days after maturity, being relatively uniform in size and maturity throughout the tree and having good handling and shipping quality. The tree having a winter chilling requirement of approximately 850 hours at or below 45° F. In comparison to its maternal proprietary nectarine parent (32RB351), the fruit of the new variety has firmer flesh with a mild, sweet, sub-acid flavor compared to acidic and is approximately 5 days later in maturity. In comparison to its pollen parent, 'Honey Royale' (U.S. Plant Pat. No. 12,008), the flesh of the new variety is similar in flavor and eating quality and is approximately 24 days later in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, 6 years of age, its flowers, foliage and fruit, as based on observations of 6 year old specimens grown near Modesto, Calif., with color in accordance with Munsell Book of Color.

Tree:

*Size.*—Large, normal for nectarine trees. Pruned to 3 to 3.5 meters in height for economical harvesting of fruit. Average spread 3 meters, varies with different cultural practices.

*Vigor.*—Vigorous, tree growth of 1.5 to 2 meters in height the first growing season. Varies with soil type, fertility, climatic conditions and cultural practices.

*Form.*—Upright, usually pruned to vase shape.

*Branching habit.*—Upright, crotch angle approximately 35°, increases with heavy crop load.

*Productivity.*—Productive, normal thinning and spacing of fruit necessary for desired market size fruit. Fruit set varies with climatic conditions during bloom period.

*Bearer.*—Regular. Adequate fruit set 4 consecutive years. No alternate bearing observed.

*Fertility.*—Self fertile.

*Density.*—Medium dense. Pruning to vase shape desirable for sunlight penetration to enhance fruit color and health of fruit wood.

*Hardiness.*—Tree grown in USDA Hardiness Zone 9. Hardy in all stone fruit growing areas of California. Winter chilling requirement approximately 850 hours at or below 45° F.

Trunk:

*Size.*—Medium to large. Average circumference 45.7 cm at 27.9 cm above ground on a 6 year old tree.

*Stocky.*—Medium stocky.

*Texture.*—Medium shaggy, roughness increases with age.

*Color.*—Varies from 10YR 6/2 to 5.5Y 6/2.

Branches:

*Size.*—Medium, normal for nectarine trees. Average circumference 23.3 cm at 1.2 meters above ground. Crotch angle approximately 35°, increases with crop load.

*Surface texture.*—New growth smooth, becoming rough with age.

*Lenticels.*—Average number 25 in a 25.8 square cm area. Average length 3.9 mm. Average width 1.4 mm. Color varies from 5YR 5/10 to 7.5YR 6/10.

*Colors.*—New growth varies from 2.5GY 6/6 to 2.5GY 4/4. Old growth varies from 5YR 3/4 to 7.5YR 3/4, varies with age of growth.

Leaves:

*Size.*—Large. Average length 143.7 mm. Average width 44.7 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 10.3 mm. Average width 1.8 mm. Color varies from 5GY 5/6 to 5GY 4/4. Longitudinally grooved. Surface — glabrous.

*Glands.*—Type — reniform. Size — large. Average length 1.4 mm. Average diameter 1.1 mm. Average number 2, varies from 1 to 4. Located primarily on base of leaf blade and upper portion of petiole. Color varies from 5GY 5/6 to 5GY 4/4.

*Color.*—Upper surface varies from 2.5GY 3/4 to 2.5GY 3/2. Lower surface varies from 5GY 4/4 to 5GY 3/4. Midvein color varies from 2.5GY 6/4 to 5GY 6/4.

Flower buds:

*Size.*—Large. Average length 17.5 mm. Average diameter 9.4 mm.

*Hardiness.*—Hardy with respect to California winter climates in stone fruit growing areas. Grown in USDA Hardiness Zone 9.

*Form.*—Conical, becoming elongated just before opening.

*Pedicel.*—Average length 4.3 mm. Average width 1.2 mm. Color varies from 2.5GY 6/8 to 5GY 6/8.

*Color.*—Varies from 5RP 8/6 to 5RP 7/10.

Flowers:

*Size.*—Large, showy. Average height 20.6 mm. Average diameter 39.7 mm.

*Petals.*—Number 5, alternately arranged to sepals. Form — orbicular, apex rounded, base narrows at point of attachment. Average length 21.5 mm. Average width 22.5 mm. Margin — sinuate, slightly cupped. Both upper and lower surfaces glabrous. Color varies from 5RP 8/6 to 7.5RP 8/6.

*Sepals.*—Number 5, alternately arranged to petals. Shape — ovate, apex rounded. Average length 5.6 mm. Average width 5.1 mm. Upper surface glabrous. Lower surface pubescent. Color — upper surface varies from 5GY 6/6 to 5GY 5/6. Lower surface varies from 2.5R 3/4 to 5R 2/6.

*Stamens.*—Average number 44 per flower. Average filament length 15.5 mm. Filament color varies from N 9.5/ (white) to 5RP 9/2, darkens with age. Anther color varies from 5R 4/8 to 7.5R 4/12.

*Pollen.*—Self fertile. Color varies from 2.5Y 7/10 to 5Y 7/10.

*Pistil.*—Number — normally one. Surface — glabrous. Average length 19.3 mm. Position of stigma average of 1.3 mm above anthers. Color varies from 2.5GY 9/6 to 2.5GY 8/6.

*Fragrance.*—Slight to moderate fragrance, varies with age of flower.

*Blooming period.*—Date of First Bloom Feb. 27, 2005. Date of Petal Fall Mar. 10, 2005, varies slightly with climatic conditions.

*Color.*—Varies from 5RP 8/6 to 5RP 7/8.

*Number of flowers per flower bud.*—One.

*Pedicel.*—Average length 4.5 mm. Average width 1.2 mm. Color varies from 5GY 7/6 to 5GY 5/6.

Fruit:

*Maturity when described.*—Firm ripe.

*Date of first picking.*—Aug. 5, 2005.

*Date of last picking.*—Aug. 11, 2005, varies slightly with climatic conditions.

*Size.*—Large. Average diameter axially 66.6 mm. Average transversely in suture plane 67.7 mm. Average weight 170.4 grams, varies slightly with fertility of the soil, amount of thinning and climatic conditions.

*Form.*—Globose.

*Suture.*—Shallow, extends from base to apex.

*Ventral surface.*—Nearly smooth.

*Apex.*—Slightly retuse, varies from round to slightly retuse.

*Base.*—Retuse.

*Cavity.*—Rounded to slightly elongated in suture plane. Average depth 6.8 mm. Average diameter 17.0 mm.

Stem:

*Size.*—Small. Average length 7.7 mm. Average diameter 3.8 mm.

*Color.*—Varies from 2.5GY 5/8 to 5GY 5/6.

Flesh:

*Ripens.*—Evenly.

*Texture.*—Firm, meaty.

*Fibers.*—Few, small, tender.

*Firmness.*—Firm, comparable to most commercial nectarine varieties.

*Aroma.*—Moderate.

*Amydgalin.*—Undetected.

*Eating quality.*—Excellent.

*Flavor.*—Excellent, mild, sweet, sub-acid flavor.

*Juice.*—Moderate amount, enhances flavor.

*Brix.*—Average 13.2°, varies slightly with amount of fruit per tree and climatic conditions.

*Color.*—Varies from 5Y 7/6 to 5Y 8/8 with 2.5R 3/10 bleeding into flesh from pit cavity. Pit cavity color varies from 5R 3/10 to 7/5R 3/10.

Skin:

*Thickness.*—Medium.

*Surface.*—Smooth.

*Down.*—Wanting.

*Tendency to crack.*—None.

*Color.*—Ground color varies from 5Y 8/10 to 5Y 7/6. Nearly overspread with color varying from 5R 3/8 to 7.5R 3/10.

*Tenacity.*—Tenacious to flesh.

*Astringency.*—None.

Stone:

*Type.*—Freestone.

*Size.*—Large. Average length 38.2 mm. Average width 26.5 mm. Average thickness 21.1 mm.

*Form.*—Ovoid.

*Base.*—Usually rounded, varies from rounded to flat.

*Apex.*—Pointed. Average length 4.6 mm.

*Surface.*—Pitted throughout, pits vary from round to elongated.

*Sides.*—Unequal, with one side extending further from suture plane.

*Ridges.*—Several high, narrow ridges extending from base toward apex, one ridge on each side of suture.

*Tendency to split.*—None.

*Color.*—Varies from 2.5YR 3/4 to 5YR 3/6, when dry.

Kernal:

*Size.*—Medium to large.

*Form.*—Ovate.

*Taste.*—Bitter.

*Viability.*—Viable, complete embryo development.

*Size.*—Large. Average length 19.1 mm. Average width 11.4 mm. Average thickness 6.8 mm.

*Skin color.*—Varies from 5Y 8.5/6 to 5Y 8/6 when dry.

Use: Dessert.

*Market.*—local and long distance.

Keeping quality: Good, held firm in cold storage 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, California, no particular plant/fruit disease resistance or susceptibility has been observed. Any variety or selection observed during indexing of plant characteristics with abnormal fungus, bacterial, virus or insect susceptibility is destroyed. and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described, characterized by its large size, vigorous, upright growth and being a productive and regular bearer of large, yellow flesh, freestone fruit, having a mild, sweet, sub-acid flavor with excellent eating quality; the fruit is further characterized by its attractive red skin color, having firm flesh with good shipping and storage quality and in comparison to the fruit of its proprietary maternal parent (32RB351), the new variety has flesh with a mild, sweet, sub-acid flavor compared to acidic type flesh and is approximately 5 days later in maturity.

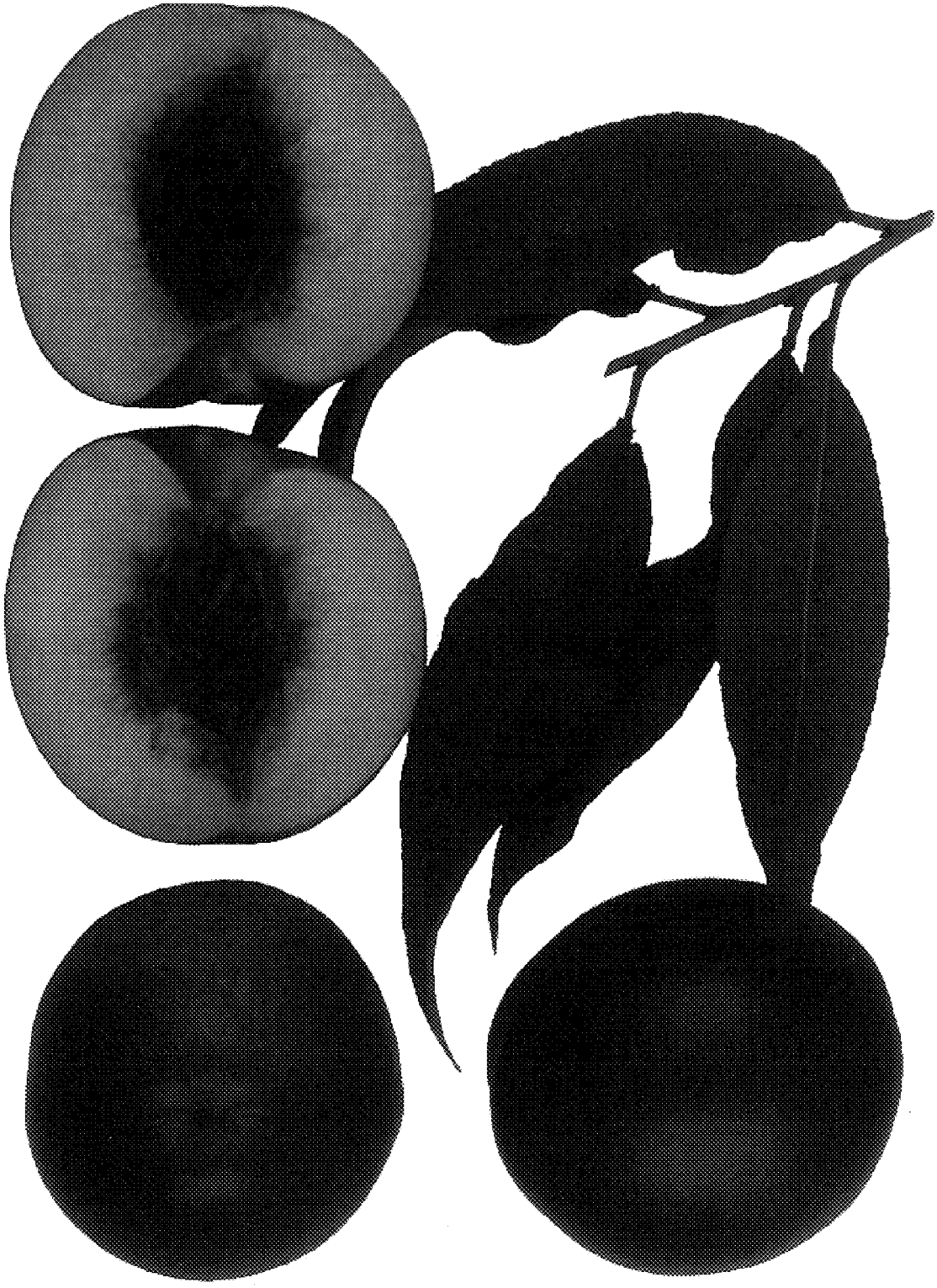

* * * * *